United States Patent
Mohamed et al.

(10) Patent No.: US 12,180,245 B1
(45) Date of Patent: Dec. 31, 2024

(54) SEPARATION AND IDENTIFICATION OF MYRICETIN-3-OGALACTOSIDE FROM CASUARINA GLAUCA

(71) Applicant: KING FAISAL UNIVERSITY, Al-Ahsa (SA)

(72) Inventors: Maged Elsayed Mohamed, Al-Ahsa (SA); Nancy Safwat Younis, Al-Ahsa (SA); Bandar Essa Eldubiab, Al-Ahsa (SA); Azza M. El Shafae, Zagazig (EG); Nora Tawfeek, Zagazig (EG); Eman Fikry, Zagazig (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/395,180

(22) Filed: Dec. 22, 2023

(51) Int. Cl.
*A61K 36/185* (2006.01)
*C07H 1/08* (2006.01)
*C07H 17/07* (2006.01)

(52) U.S. Cl.
CPC ............ *C07H 1/08* (2013.01); *A61K 36/185* (2013.01); *C07H 17/07* (2013.01); *A61K 2236/15* (2013.01); *A61K 2236/333* (2013.01); *A61K 2236/51* (2013.01)

(58) Field of Classification Search
None
See application file for complete search history.

(56) References Cited

PUBLICATIONS

Revilla et al. (1998) J. Agric. Food Chem. 46: 4592-4597. (Year: 1998).*
Azevedo et al. (2015) J. Nat. Med. 69: 487-493. (Year: 2015).*
Campos et al. (2013) J. Ethnopharmacology, 150: 270-274. (Year: 2013).*
Xu Z, He WQ, Liu CS, Kong JQ. "Enzymatic synthesis of myricetin 3-O-galactoside through a whole-cell biocatalyst", Chin Herb Med. Oct. 16, 2020;12(4):384-389.
Wu C, He L, Zhang Y, You C, Li X, Jiang P, Wang F. "Separation of flavonoids with significant biological activity from Acacia mearnsii leaves", RSC Adv. Mar. 20, 2023;13(13):9119-9127.
Park, BJ., Matsuta, T., Kanazawa, T. et al. "Phenolic compounds from the leaves of Psidium guajava", I. Hydrolysable tannins and benzophenone glycosides. Chem Nat Compd 47, 632 (2011).
World Health Organization, "Medicinal Plants in Papua New Guinea", 2009.
Rajalakshmi I. et al. "Review on hepatoprotective medicinal plants", European Journal of Complementary and Alternative Medicine. 2014;1(1):24-30.
LaouéJ, Fernandez C, Ormeño E. "Plant Flavonoids in Mediterranean Species: a Focus on Flavonols as Protective Metabolites under Climate Stress. Plants (Basel)". Jan. 10, 2022;11(2):172.
Ghitti, E.; Rolli, E.; Crotti, E.; Borin, S. "Flavonoids Are Intra-and Inter-Kingdom Modulator Signals", Microorganisms 2022, 10, 2479.

* cited by examiner

*Primary Examiner* — Russell G Fiebig
(74) *Attorney, Agent, or Firm* — Nath, Goldberg & Meyer; Joshua B. Goldberg

(57) ABSTRACT

The disclosure of the present patent application relates generally to the separation and identification of myricetin-3-O-galactoside from *Casuarina glauca* Sieber branchlets.

4 Claims, 5 Drawing Sheets

SEPARATION AND IDENTIFICATION OF MYRICETIN-3-OGALACTOSIDE FROM CASUARINA GLAUCA

BACKGROUND

1. Field

The disclosure of the present patent application relates generally to the separation and identification of myricetin-3-O-galactoside from *Casuarina glauca* Sieber.

2. Description of the Related Art

*Casuarina glauca* Sieber, (*C. glauca*), commonly known as the swamp she oak, is a species of the family Casuarinaceae. *Casuarina* species are tropical and subtropical trees native to Australia, southeastern Asia, and islands of the western Pacific Ocean, and wildly cultivated in Egypt. *Casuarina* trees are commonly used as windbreaks for rehabilitating and stabilizing dunes, as ornamental trees, and for timber and firewood production. Extracts from *C. glauca* exhibit weak antibacterial activity, which could be related to their components of polyphenols and condensed tannins, such as casuarictin, casuarinin and casuariin, which were previously isolated from *C. glauca*.

Casuarictin, an ellagitannin, has emerged as a promising herbal therapeutic against Alzheimer's disease. Ethyl acetate fractions from *C. glauca* bark had the highest antibacterial activities, which could also be attributed to other components such as formic acid, 1 methylethyl ester, the benzyl benzoate and 1,2 benzenediol or pyrocatechol.

Myricetin-3-O-galactoside is a flavonoid that has been found in some plants such as *Myrtus communis*, and it has diverse biological activities. It exhibits xanthine oxidase inhibition activity and shows cytotoxic activity in many cell lines. The compound also inhibits hydrogen peroxide induced malondialdehyde (MDA) formation and displays anti-inflammatory activity.

Thus, a method for separation and identification of myricetin-3-O-galactoside from plant materials is desired.

SUMMARY

The present subject matter relates to the separation and identification of myricetin-3-O-galactoside from certain plants, including by way of non-limiting example, *Casuarina glauca* Sieber.

The present subject matter provides a method for effective separation and identification of myricetin-3-O-galactoside from *Casuarina glauca* Sieber.

In one embodiment, the present subject matter relates to a process for separating myricetin-3-O-galactoside from a plant comprising: providing fresh branchlets of the plant; shade drying and powdering the branchlets to obtain a plant powder; soaking the plant powder in 70% ethyl alcohol in water to obtain a plant extract; concentrating the plant extract to obtain a residue; dissolving the residue in a mobile phase to obtain a solution; mixing and sonicating the solution; followed by centrifuging the solution and subjecting it to separation to obtain myricetin-3-O-galactoside. In certain embodiments, the plant may be *Casuarina glauca* Sieber.

In a further embodiment, the present subject matter relates to a pharmaceutically acceptable composition comprising a therapeutically effective amount of a myricetin-3-O-galactoside composition as described herein and a pharmaceutically acceptable carrier.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION OF THE PREFERRED EMBODIMENTS

Figure 1A:
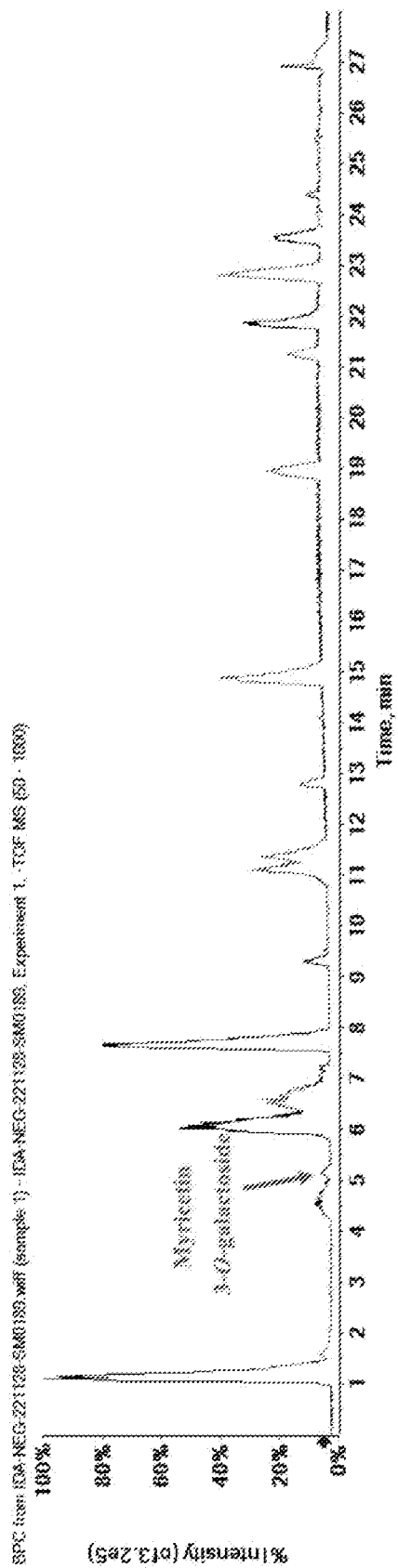
FIGS. 1A-C depict separation chromatograms of *Casuarina glauca* branchlets extract, showing myricetin 3-O-galactoside, (FIG. 1A) BCP, (FIG. 1B) TIC, and (FIG. 1C) XIC chromatograms.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, "myricetin-3-O-galactoside" refers to a glycosyloxyflavone that is myricetin with a beta-D-galatosyl residue attached at position 3 and has the structure:

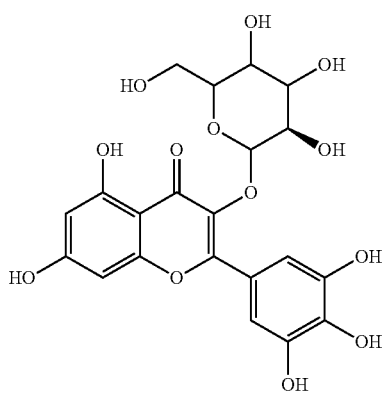 [SMILES: O=c1c(OC2OC(CO)C(O)C(O)[C@H]2O)c(-c2cc(O)c(O)c(O)c2)oc2cc(O)cc(O)c12]

This compound is alternatively known as myricetin 3-galactoside, myricetin 3-O-beta-D-galactopyranoside, and the like.

As used herein, "*Casuarina glauca* Sieber" may refer to *Casuarina glauca*, swamp she-oak, swamp buloke, marsh sheoak, grey she-oak, or the like. *C. glauca* is a species of flowering plant endemic to eastern Australia.

The present subject matter relates to the separation and identification of myricetin-3-O-galactoside from certain plants. More specifically, it provides a method for effective separation and identification of the myricetin-3-O-galactoside from *Casuarina glauca* Sieber.

In one embodiment, the present subject matter relates to a process for separating myricetin-3-O-galactoside from a plant comprising: providing fresh branchlets of the plant; shade drying and powdering the branchlets to obtain a plant powder; soaking the plant powder to obtain a plant extract; concentrating the plant extract to obtain a residue; dissolving the residue in mobile phase to obtain solution; mixing and sonicating the solution; followed by centrifuging the solution, and subject it for separation to obtain myricetin-3-O-galactoside.

In an embodiment, the fresh branchlets are obtained from *Casuarina glauca* Sieber.

In an embodiment, the process for obtaining myricetin-3-O-galactoside may further comprise soaking 300 g of plant powder obtained from *Casuarina glauca* Sieber branchlets, with 70% ethyl alcohol.

In any embodiment, the soaking may be repeated once, twice, three, four, five, or more times. In one embodiment in this regard, the soaking may be repeated in three successive portions of 1 L each.

In an embodiment of the present processes, the residue may be dissolved in about 1 ml of a mobile phase solution comprising water:methanol:acetonitrile (50:25:25).

In an embodiment of the present processes, mixing and sonicating the aqueous mixture may include vortexing for about 2 minutes and subjecting the aqueous mixture to ultrasonication for about 10 minutes.

In an embodiment of the present processes, the aqueous mixture may be centrifuged for about 10 minutes at about 1,000 rpm.

In another embodiment, the present subject matter relates to a pharmaceutically acceptable composition comprising a therapeutically effective amount of the myricetin-3-O-galactoside composition as described herein and a pharmaceutically acceptable carrier, excipient, or vehicle. In certain embodiments in this regard, the pharmaceutically acceptable carrier can be suitable for injection to a human.

Non-limiting examples of suitable excipients, carriers, or vehicles useful herein include liquids such as water, saline, glycerol, polyethylene glycol, hyaluronic acid, ethanol, and the like. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for a disease, disorder, or condition as described herein. Administration of the compounds or pharmaceutical compositions thereof can be by any method that delivers the compounds systemically and/or locally. These methods include oral routes, parenteral routes, injection routes, intraduodenal routes, and the like. In an embodiment, the present methods involve injection routes of administration.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a disease, disorder, or condition herein, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject.

Methods of Use

The present subject matter involving myricetin-3-O-galactoside has valuable pharmaceutical properties, which makes it commercially utilizable. Accordingly, the present subject matter further relates to a method of treating a disease, disorder, or condition in a patient, comprising administering to a patient in need thereof a therapeutically effective amount of the pharmaceutically acceptable composition as described herein.

The following examples relate to obtaining, testing, and/or analyzing as described herein.

EXAMPLES

Example 1

Fresh branchlets of *Casuarina glauca* Sieb. ex Spreng. Were collected in April 2022 from the Experimental Farm, Agriculture Research Center (ARC), Giza, Egypt. The plant was taxonomically verified by Eng. Therese Labib Youssef, Plant Taxonomy Consultant at the Ministry of Agriculture and Ex Manager at El Orman Botanical Garden, Giza; and Prof. Ahmed Abd El Dayem, Professor at Forestry Department, Horticulture Research Institute, Giza, Egypt. The shade dried powdered branchlets (300 g) were soaked with 70% ethyl alcohol for extraction, in three successive portions (1 L each) each). The extract was concentrated by evaporation under reduced pressure to provide 60 g of viscous residue.

Figure 1B:
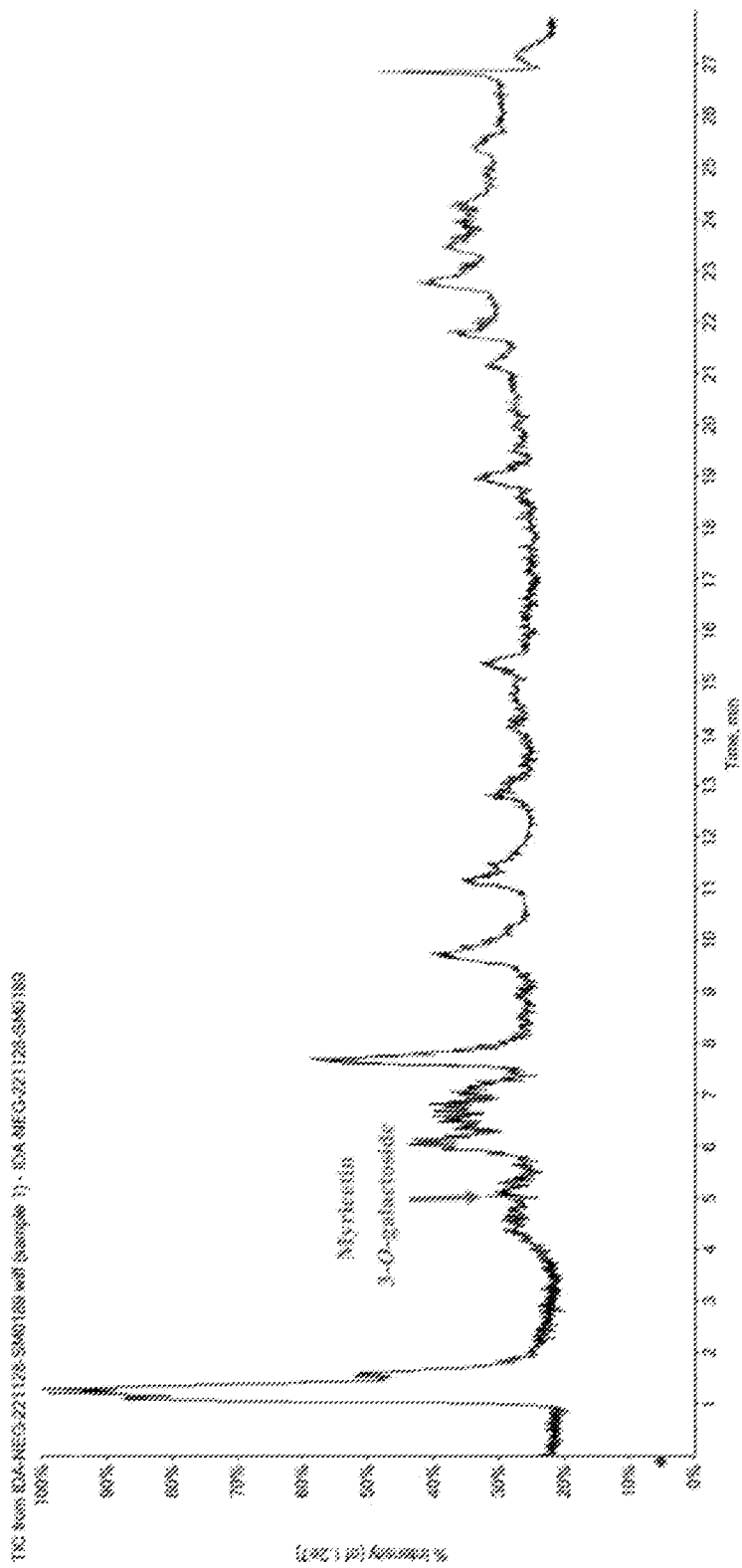
Figure 1C:
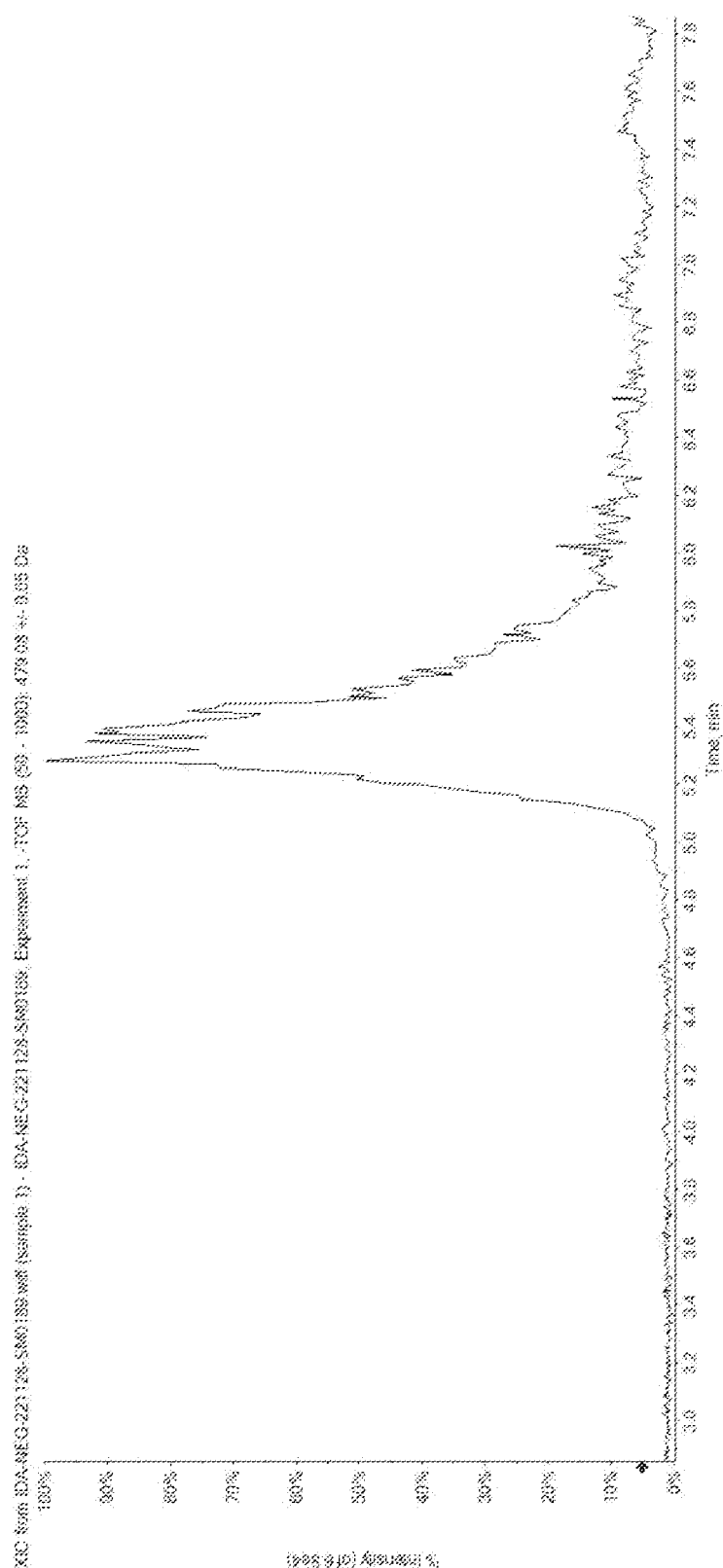

50 mg of the ethanolic extract residue was dissolved in 1 mL of the mobile phase solution (water:methanol:acetonitrile (50:25:25)), vortexed for 2 minutes, subjected to ultrasonication for 10 minutes, and then centrifuged for 10 minutes at 1000 rpm. 50 µl of the resulting sample solution was diluted 20 times with mobile phase solution to a volume of 1000 µl. 10 µl of the resulting solution was analyzed via LC-ESI-MS/MS in negative mode, utilizing the ExionLC™ AD UPLC instrument and a TripleTOF 5600+Time-of-Flight Tandem Mass Spectrometer (AB SCIEX). In-line filter disks (0.5 µm×3.0 mm, Phenomenex®, Torrance, USA) was implemented as pre-column, and X select HSS T3 (2.5 µm and 2.1 mm×150 mm, column temperature 40° C., flow rate 0.3 mL/min Waters®, Milford, MA, USA) was used as the analytical column. The mobile phase was buffer A (5 mM ammonium format buffer pH 8 and 1% methanol) and buffer B (100% acetonitrile). The elution process was initiated with a ratio of 90% (A): 10% (B) for the first 20 minutes, followed by a transition to a ratio of 10% (A): 90% (B) from 21 to 25 minutes, and finally a return to the initial ratio for the last 3 minutes (total time 28 minutes). Myricetin 3-O-galactoside was separated at the retention time of 5.360 minutes, Table 1, and as shown in FIGS. 1A-1C.

TABLE 1

LC-ESI-MS/MS of myricetin 3-O-galactoside in negative mode.

| Rt. | [M − H]$^-$ | MS$_2$ fragments (m/z) | Identification | Class |
|---|---|---|---|---|
| 5.360 | 479.085 | 479, 317, 316, 271, 287, 179 | Myricetin 3-O-galactoside | Flavonol glycoside |

Figure 2A:
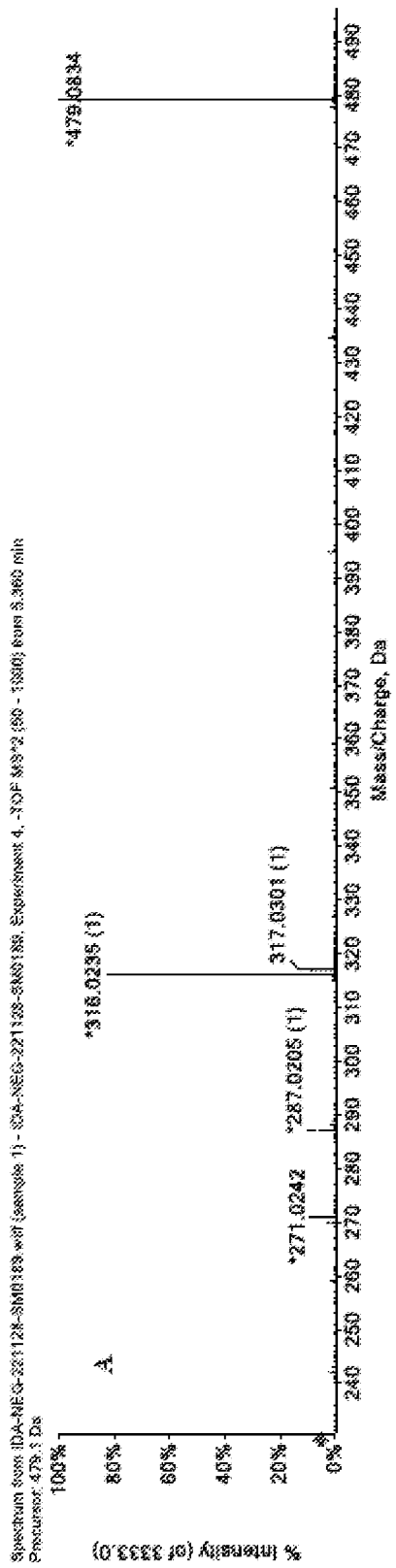
FIGS. 2A-2B depict mass spectrograms of myricetin 3-O-galactoside showing the molecular ion peak and daughter ions.
Figure 2B:
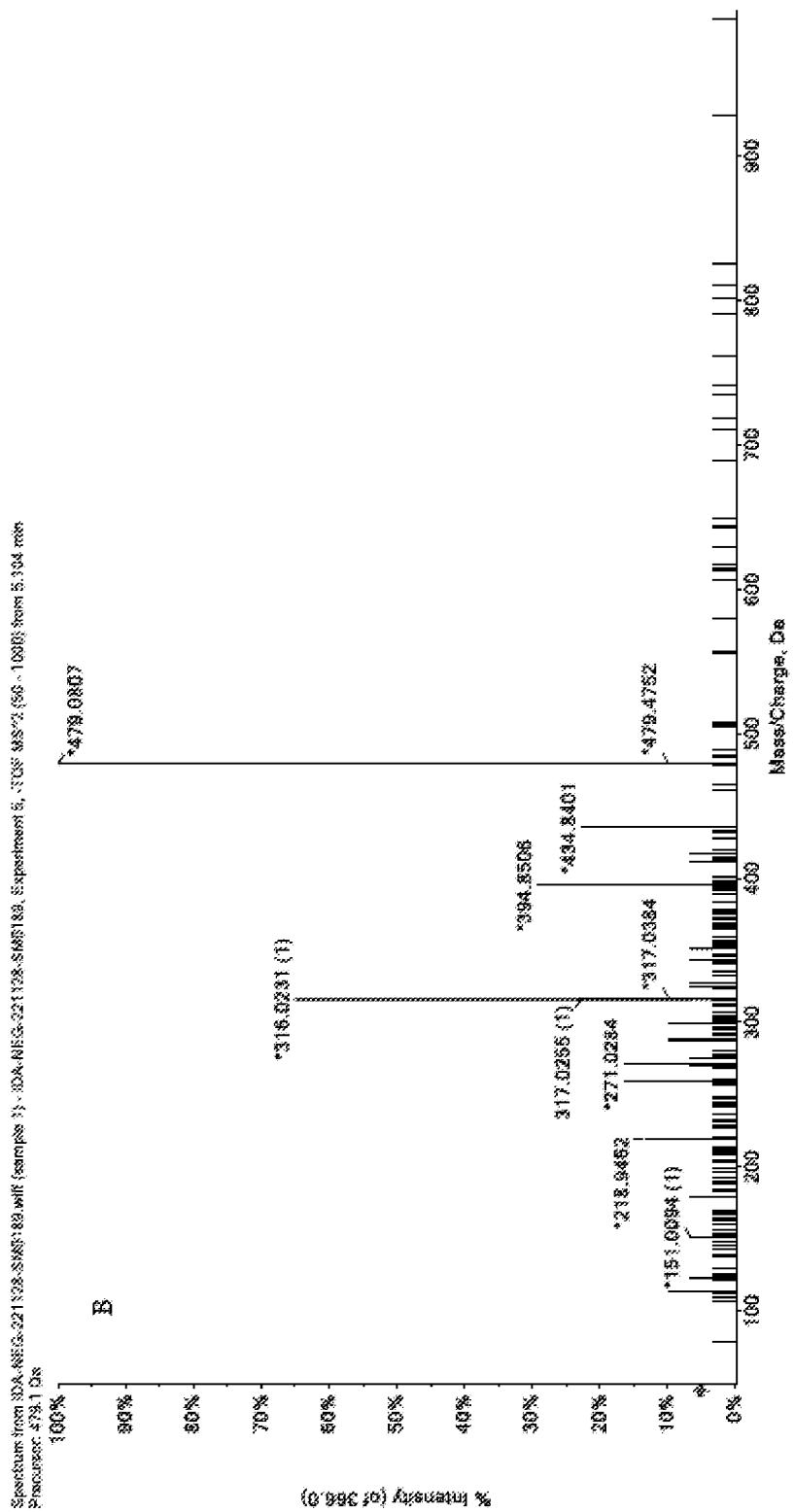

In order to tentatively identify myricetin 3-O-galactoside, the Peak View™ software was employed to conduct a comparative analysis of retention time (RT) and mass-to-charge ratio (m/z) values obtained through MS and MS/MS, using parameters mentioned in Table 1, and shown in FIGS. 2A-2B.

FIGS. 2A-2B show the mass spectrometer of Myricetin 3-O-galactoside, including the molecular ion peak and the daughter ions. The compound was identified based on its molecular ion (m/z 479.085) and daughter ion fragment (m/z 479, 317, 316, 271, 287, 179) and in accordance with Jelaca, S. et al. (Beyond Traditional Use of *Alchemilla vulgaris*: Genoprotective and Antitumor Activity In Vitro. Molecules, 2022 27 (3): p. 8113).

It is to be understood that the myricetin-3-O-galactoside, use/application, and properties thereof are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the instant subject matter compounds.

We claim:

1. A process for separation and identification of myricetin-3-O-galactoside comprising:
   providing fresh branchlets of a *Casuarina glauca* plant;
   shade drying and powdering the fresh branchlets to obtain a *Casuarina glauca* plant powder;
   soaking 300 g of the *Casuarina glauca* plant powder with 70% ethyl alcohol to obtain a *Casuarina glauca* plant extract;
   concentrating the *Casuarina glauca* plant extract to obtain a residue;
   dissolving the residue to obtain an aqueous mixture;
   mixing and sonicating the aqueous mixture;
   centrifuging the aqueous mixture to obtain a supernatant;
   separating myricetin-3-O-galactoside from the supernatant; and
   wherein the soaking step is repeated three times in successive portions of 1 L of the 70% ethyl alcohol.

2. The process of claim 1, wherein the plant is *Casuarina glauca* Sieber.

3. The process of claim 1, wherein the supernatant is about 1 ml of a mobile phase solution comprising water:methanol:acetonitrile (50:25:25).

4. The process of claim 1, wherein the mixing and sonicating step comprises:
   vortexing the aqueous mixture for about 2 minutes; and
   subjecting the aqueous mixture to ultrasonication for about 10 minutes.

* * * * *